(12) United States Patent
Amberg-Schwab et al.

(10) Patent No.: US 6,423,128 B1
(45) Date of Patent: Jul. 23, 2002

(54) COATING MATERIAL ON THE BASIS OF LIQUID CRYSTALLINE INORGANIC/ORGANIC HYBRID POLYMERS

(75) Inventors: Sabine Amberg-Schwab, Erlabrunn; Manfred Hoffmann, Wurzburg, both of (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 09/244,664

(22) Filed: Feb. 4, 1999

(30) Foreign Application Priority Data

Feb. 4, 1998 (DE) .......................... 198 04 388

(51) Int. Cl.$^7$ ................... C09D 183/04; C09D 183/06; C09D 183/10; C08G 77/06; C08G 77/14; C08L 83/04; C09K 19/38; C09K 19/40

(52) U.S. Cl. ........................ 106/287.13; 106/287.16; 252/299.01; 428/1.23; 428/1.52; 428/405; 522/91; 522/99; 524/860; 524/863; 525/102

(58) Field of Search .............. 252/299.01, 299.62, 252/299.4; 106/287.13, 287.16; 428/1.23, 1.52, 405; 522/91, 99; 524/860, 863; 525/102

(56) References Cited

U.S. PATENT DOCUMENTS 5,605,649 A * 2/1997 Stohrer et al. ......... 252/299.01

FOREIGN PATENT DOCUMENTS

| DE | 3119459 A1 | 5/1981 |
|----|------------|--------|
| DE | 3828098 A1 | 3/1990 |
| DE | 4025215 A1 | 2/1992 |
| DE | 4303570 A1 | 8/1994 |
| EP | 312280 *   | 4/1989 |
| EP | 358011 B1  | 3/1990 |
| EP | 471301 A2  | 2/1992 |
| EP | 610831 B1  | 8/1994 |

OTHER PUBLICATIONS

"Gas Permeation Through A Side–Chain Liquid–Crystalline Polysiloxane–Based Membrane," Deng–Shan Chen, Ging–Ho Hsiue, Makromol. Chem. 192, pp. 2021–2029 (1991).

"Synthesis and Properties of Side Chain Liquid Crystal Polysiloxanes," G.W. Gray, School of Chemistry, The University of Hull, Hull HU6 7RX, UK, pp. 106–129, 1991.

"Barriereschichten Für Verpackungs–Materialien," S. Amberg–Schwab, M. Hoffmann, and H. Bader, Kunstsoffe, vol. 86 (1996), No. 5, pp. 660–663.

"Kristalline Flüssigkeiten. Ein Vierter Aggregatzustand?," Dr. Albrecht Mannschreck, Chemiker–Zig./Chem. Apparatur, 92. Jahrgang (1968) Nr. 3, pp. 69–72.

* cited by examiner

Primary Examiner—Shean C. Wu
(74) Attorney, Agent, or Firm—Barnes & Thornburg

(57) ABSTRACT

The invention pertains to a coating material on the basis of liquid crystalline polysiloxanes which is obtained via the co-condensation of mesogenous silanes and/or polysiloxanes, that are capable of being hydrolyzed, with sols.

11 Claims, 1 Drawing Sheet

$C_{20}H_{26}O_6Si$
390.50

Silane 1

$C_{20}H_{23}NO_5Si$
385.49

Silane 2

$C_{20}H_{26}O_7Si$
406.50

Silane 3

$C_{40}H_{64}O_6Si$
669.03

Silane 4

COATING MATERIAL ON THE BASIS OF LIQUID CRYSTALLINE INORGANIC/ORGANIC HYBRID POLYMERS

CROSS REFERENCE TO RELATED APPLICATIONS

This application claims priority under 35 U.S.C. §119(a) to German Application Serial No. 198 04 388.0, filed Feb. 4, 1998.

BACKGROUND AND SUMMARY OF THE INVENTION

Inorganic/organic hybrid polymers have been known since about 1980. The principle structure of these materials is derived from the network structure of silica glass with Si—O—Si bonds. Their synthesis takes place using the sol/gel process via the controlled hydrolysis and condensation of alkoxysilanes. If metal oxides are also included in the sol/gel process, then the silicate network can be modified in a controlled manner.

An organic network can also be assembled as a result of the polymerization of organo-functional groups which can be introduced into the material via organo-alkoxysilanes. Reactive methacrylate groups, epoxy groups or vinyl groups can be polymerized in this way by means of thermal or, as the case may be, photochemical induction.

DE 43 03 570 describes hybrid polymers which are designated ORMOCER® compounds.

Because of their possible breadth of structural variation, a series of different material properties can be set up and combined in inorganic/organic hybrid polymers (e.g. abrasion resistance, corrosion protection properties, barrier properties, etc.). Barrier properties of inorganic/organic hybrid polymers have been researched in regard to the permeation through them of oxygen, water vapor and hydrocarbons which derive from various types of different aroma-promoting substances translator: aromatic organic compounds?. It has been possible to detect a good to very good barrier property in all cases (see: Arnberg-Schwab, M. Hoffmann, H. Bader: "Kunststoffe 86", 1996, 5, pp. 660–664).

Approximately 3,000 organic compounds, to which a specific state of aggregation is assigned on the basis of their characteristic properties, form part of the group of liquid crystalline compounds. The phenomena of liquid crystalline compounds were observed in 1888 in cholesterol benzoate which actually melted at 145.5° C. but which remained cloudy and turbid. The melt suddenly became clear only at 178.5° C. On cooling, the effects occurred in the reverse sequential order (Mannschreck: "Chemiker-Zeitung 92", 1968, pp. 69–72).

Liquid crystalline compounds have been on the market since 1904 but the principles of their structure became recognized only much later. Thermotropic liquid crystalline compounds, which are obtained by heating crystals above their melting point, exhibit properties which lie between those of the liquid state and those of the solid state: they exhibit the mobility of liquids, which are generally isotropic, and also the optical anisotropy of crystals. Whereas in liquids, the molecules move freely in the three dimensions and are capable of rotating about three mutually vertically oriented axes and whereas in the solid state, by contrast, the molecules are fixed and are not able to rotate, in the liquid crystalline state, however, the molecules are capable of translation movements. The crystal lattice breaks down at the crystalline/liquid crystalline transition point but the molecules retain a preferred orientation: they become aligned parallel to one another. Liquid crystals lose their optical anisotropy property (turbidity as a consequence of the scattering of incident rays of light, double refraction and diffraction phenomena) only at the liquid crystalline/liquid transition point.

Liquid crystalline polymers (LCP) differ e.g. in regard to their crosslinking structures (backbones). Polymers with acrylate main chains, methacrylate main chains and siloxane main chains are the most common. A review regarding such compounds is given in Gray, G. W.: Synthesis and properties of side chain liquid crystal polysiloxanes, in "Side Chain Liquid Crystal Polymers", 1992, pp. 106–129.

However, a disadvantageous feature of the liquid crystalline polymers (LCP) of the prior art is that although these do have improved barrier properties, especially with respect to oxygen, compared to non-liquid crystalline polysiloxanes, their barrier properties are not adequate for many applications. Thus the substrates, that are coated with these LCP, are still not satisfactory in regard to physical properties and, especially, in regard to scratch resistance.

Starting out from here, the problem for the present invention is therefore to propose new coating materials which exhibit good adhesion and excellent abrasion resistance and scratch resistance in addition to good barrier properties.

The problem is solved by the characterizing features of claim 1. The subsidiary claims show further advantageous forms of embodiments.

DETAILED DESCRIPTION OF THE INVENTION

Figure 1:
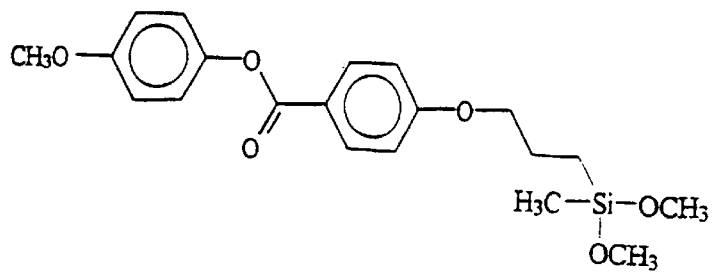
FIG. 1 shows mesogenous silanes capable of being hydrolyzed (silan=silane).
Figure 1:
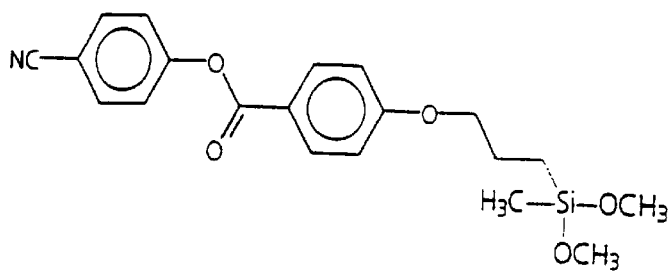
Figure 1:
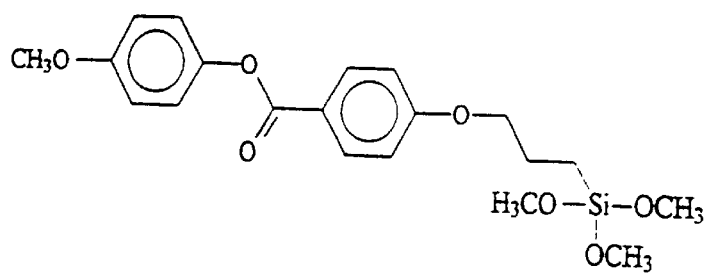
Figure 1:
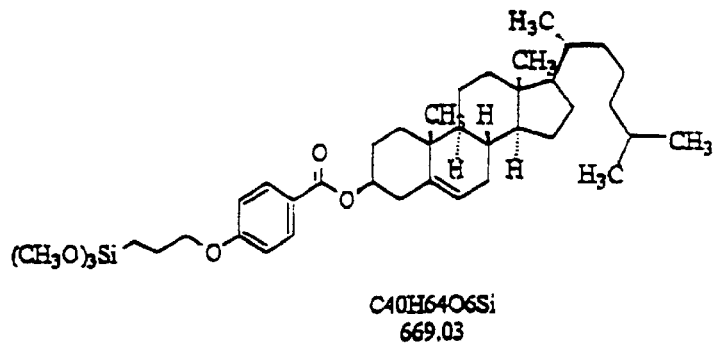

The coating materials in accordance with the invention accordingly comprise a condensate of so-called ORMOCER sols—or, as the case may be, their starting silanes—with mesogenous silanes and/or polysiloxanes that are capable of being hydrolyzed. Surprisingly, it has been found that coating materials, that are prepared in this way, exhibit distinctly better barrier properties than were previously known for liquid crystalline polysiloxanes (e.g. D. Chen, G. Hsiue; Makromol. Chem. 192; 2021–2029; 1981) or conventional ORMOCER systems (see Table 1). A feature that is also to be emphasized, especially in the case of the coating material in accordance with the invention, is that not only have the barrier properties been significantly improved, e.g. with respect to oxygen or water vapor, but that, at the same time, the properties which are known per se for ORMOCER® compounds, namely excellent adhesion to various substrates, good abrasion resistance and good scratch resistance, have also been kept intact. The coating material in accordance with the invention therefore combines the advantages of liquid crystals with the advantages of ORMOCER® coatings. It is especially advantageous that covalent linking of the mesogenous molecules to the silicate network of the inorganic/organic hybrid polymer is achieved as a result of co-condensation. The covalent linking of the mesogenous molecules is very important for barrier materials in particular, since the formation of interfaces between the ORMOCER® matrix and the liquid crystalline molecules could create additional diffusion channels for permeation.

Among the mesogenous silanes/polysiloxanes, which are capable of being hydrolyzed, those in accordance with general formula I

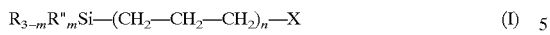
$$R_{3-m}R''_m Si\text{—}(CH_2\text{—}CH_2\text{—}CH_2)_n\text{—}X \quad (I)$$

and general formula II

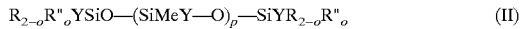
$$R_{2-o}R''_o YSiO\text{—}(SiMeY\text{—}O)_p\text{—}SiYR_{2-o}R''_o \quad (II)$$

are especially preferred. In the general formulas I and II, R=a group, which is capable of being hydrolyzed, such as hydrogen, halogen, alkoxy, acyloxy, alkylcarbonyl, alkoxycarbonyl, or $NR'_2$ with R'=hydrogen, alkyl or aryl.

R'' is a $C_1$–$C_{20}$ alkyl, either straight chain or branched, and preferably methyl or ethyl.

X=a mesogenous molecular residue, Y=—$CH_2$—$CH_2$—$(CH_2)_n$—X, m=0–2, n=1–25, o=0 or 1, p=0–500.

The mesogenous molecular residues, which are suitable for the coating material in accordance with the invention, are known as such from the prior art. A review regarding them is contained, for example, in DE 31 19 459. Especially suitable mesogenous molecular residues are: derivatives of cyclohexane such as the phenyl esters of cyclohexylcarboxylic acid, cyclohexyl phenyl esters, cyclohexyl phenyl ethers, cyclohexylbenzenes, cyclohexyl esters of cyclohexylcarboxylic acid, dicyclohexyl derivatives, derivatives of stilbene, derivatives of the phenyl ester of benzoic acid, benzylidene-aniline, derivatives of azobenzene, derivatives of azoxybenzene, alkyl derivatives and alkoxy derivatives of biphenyl, Schiff's bases, steroids such as derivatives of cholesterol and cholestane.

The synthesis of the mesogenous silanes/polysiloxanes, which are capable of being hydrolyzed, in order to carry out the sol/gel process takes place via the hydrosilylation of olefinic groups of mesogenous molecules with Si—H silanes or, as the case may be, polysiloxanes, which are capable of being hydrolyzed, in accordance with the following arrangement:

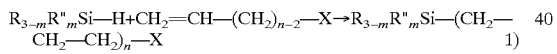
$$R_{3-m}R''_m Si\text{—}H + CH_2\text{=}CH\text{—}(CH_2)_{n-2}\text{—}X \rightarrow R_{3-m}R''_m Si\text{—}(CH_2\text{—}CH_2\text{—}CH_2)_n\text{—}X \quad 1)$$

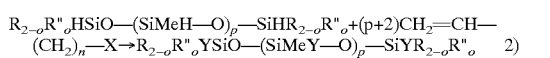
$$R_{2-o}R''_o HSiO\text{—}(SiMeH\text{—}O)_p\text{—}SiHR_{2-o}R''_o + (p+2)CH_2\text{=}CH\text{—}(CH_2)_n\text{—}X \rightarrow R_{2-o}R''_o YSiO\text{—}(SiMeY\text{—}O)_p\text{—}SiYR_{2-o}R''_o \quad 2)$$

The liquid crystalline inorganic/organic hybrid polymers (ORMOCER compounds) are obtained via the co-condensation of mesogenous silanes/polysiloxanes, which are capable of being hydrolyzed, with ORMOCER sols, or as the case may be, their starting silanes. Among the ORMOCER compounds, those that are described in DE 43 03 570 A1 are especially preferred. Further suitable examples are contained in DE 38 28 098 and DE 40 25 215 A1. Thus reference will be made explicitly to the contents of these disclosures.

There are various possibilities for co-condensation in this connection:

- pre-hydrolysis and pre-condensation of the mesogenous silane/polysiloxane, which is capable of being hydrolyzed, and addition to the ORMOCER sol;
- pre-hydrolysis and pre-condensation of the mesogenous silane/polysiloxane, which is capable of being hydrolyzed, and addition to the starting silanes, which are used for the preparation of the ORMOCER compound, and a subsequent sol/gel process;
- addition of the mesogenous silane/polysiloxane, which is capable of being hydrolyzed, to the ORMOCER sol and subsequent co-condensation;
- addition of the mesogenous silane/polysiloxane, which is capable of being hydrolyzed, to the starting silanes, which are used for the preparation of the ORMOCER compound, and subsequently a sol/gel process.

In order to prepare liquid crystalline ORMOCER layers, the transparent clear sols—analogously to the conventional ORMOCER compounds—are applied via conventional application techniques (centrifugation, doctor-bar application, rollers, . . . ) onto the carrier of the coating. The lacquer films—analogously to the conventional ORMOCER compounds—are then cured thermally or photochemically.

Covalent linking of the mesogenous molecules, via organic groups which are capable of being polymerized, to the organic network of the ORMOCER compounds is also conceivable. Thus covalent linking of the mesogenous molecules simultaneously to the two networks of the ORMOCER compounds (both the organic and the inorganic network) is also possible in principle.

In addition to their use as barrier layers, liquid crystalline ORMOCER compounds are also usable, in principle, for other applications in which liquid crystalline material properties are required. Layers with ferro-electric properties, optical-sensory properties, thermotropic properties or non-linear optical properties are conceivable here, for example. Naturally, applications are also conceivable in which typical ORMOCER properties and liquid crystalline properties are desired. Because of the ability of liquid crystalline ORMOCER systems to melt, usage in the area of powder lacquers is also conceivable.

The invention will be elucidated in more detail below by means of Examples 1 to 5 of various embodiments.

In order to prepare the materials for the Examples 1 to 5 of the various embodiments, use was made of the mesogenous silanes 1, 2, 3 and 4 which are capable of being hydrolyzed.

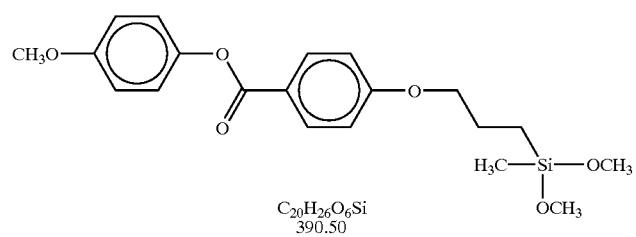

Silan 1

-continued

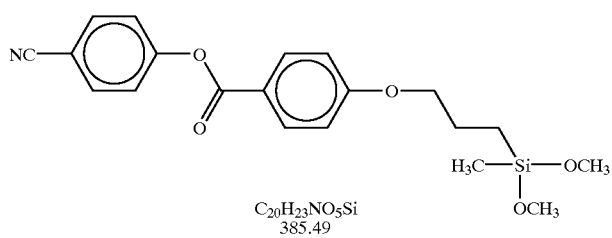

Silan 2

C$_{20}$H$_{23}$NO$_5$Si
385.49

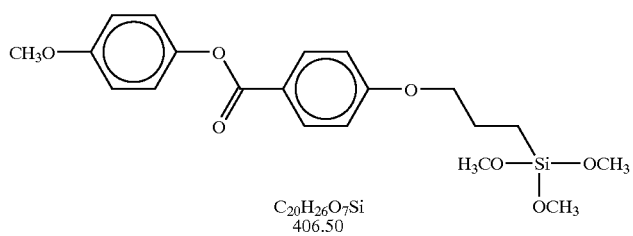

Silan 3

C$_{20}$H$_{26}$O$_7$Si
406.50

Silan 4

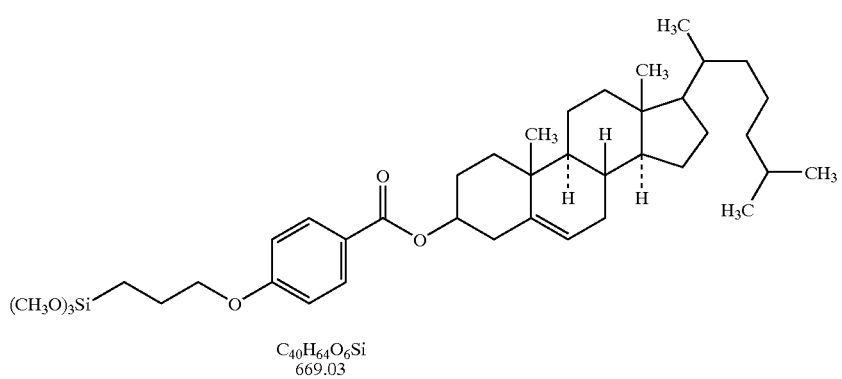

C$_{40}$H$_{64}$O$_6$Si
669.03

EXAMPLE 1

1.80 (7.50 mmol) 3-glycidoxypropyltrimethoxysilane (GLYMO), 0.03 g (0.38 mmol) N-methylimidazole and 10.0 g (150 mmol) silane 4 are dissolved in 50 ml tetrahydrofuran. 0.90 g (51.0 mmol) 0.1 HCl solution are added to the clear solution and stirred for 24 hours at 25° C. Filtration is then carried out by means of a filter (pore size 0.45 μm) and the solvent is distilled off at normal pressure.

EXAMPLE 2

2.36 g (10.0 mmol) 3-glycidoxypropyltrimethoxysilane (GLYMO), 0.04 g (0.50 mmol) N-methylimidazole and 0.27 g (15 mmol) water are stirred for 3 h at room temperature. After adding 1.52 g (5.00 mmol) (3-triethoxypropyl) succinic anhydride, the clear solution is stirred for a further hour. 20.1 g (30.0 mmol) silane 4 in 100 ml THF are now added and stirred for 24 hours at room temperature after the addition of 1.53 g (85.0 mmol) Filtration is then carried out by means of a filter (pore size 0.45 μm) and the solvent is distilled off at normal pressure.

The highly viscous resin is applied to PA6 foil by means of a spiral doctor-bar (50 μm). The layer is cured for 3 h at 130° C.

EXAMPLE 3

Sol 1: 1.00 g (2.46 mmol) silane 3 are dissolved in 10.0 g ethyl acetate and mixed with 0.13 g (7.38 mmol) 0.1 N HCl. The solution is stirred for 24 h at room temperature.

Sol 2: a sol is prepared comprising 30 mol % tetramethoxysilane, 45 mol % 3-glycidoxypropyltrimethoxysilane, 5 mol % 3-aminopropyltriethoxysilane, 10 mol % aluminum tri(sec.-butoxide) and 10 mol % zirconium tetrapropoxide. For hydrolysis, one mol of water is used, in total, per mol of alkoxy residue which is capable of being hydrolyzed. The time for hydrolysis amounts to 2 h at room temperature.

0.5 g sol 2 is slowly added, drop by drop, to sol 1 with cooling by means of ice. Filtration is then carried out by means of a filter (pore size 0.45 μm) and the solvent is distilled off at normal pressure.

The highly viscous resin is applied to PA6 foil by means of a spiral doctor-bar (50 μm). The layer is cured for 3 h at 130° C.

EXAMPLE 4

Sol 1: 1.00 g (2.56 mmol) silane 1 are dissolved in 10.0 g ethyl acetate and mixed with 0.10 g (5.12 mmol) 0.1 N HCl. The solution is stirred for 24 h at room temperature.

Sol 2: a sol is prepared comprising 30 mol % tetramethoxysilane, 45 mol % 3-glycidoxypropyltrimethoxysilane, 5 mol % 3-aminopropyltriethoxysilane, 10 mol % aluminum tri(sec.-butoxide) and 10 mol % zirconium tetrapropoxide. For hydrolysis, one mol of water is used, in total, per mol of alkoxy residue which is capable of being hydrolyzed. The time for hydrolysis amounts to 2 h at room temperature.

0.5 g sol 2 is slowly added, drop by drop, to sol 1 with cooling by means of ice. Filtration is then carried out by means of a filter (pore size 0.45 μm) and the solvent is distilled off at normal pressure.

7

The highly viscous resin is applied to PA6 foil by means of a spiral doctor-bar (50 µm). The layer is cured for 3 h at 130° C.

EXAMPLE 5

Sol 1: 1.00 g (2.58 mmol) silane 2 are dissolved in 10.0 g ethyl acetate and mixed with 0.09 g (5.18 mmol) 0.1 N HCl. The solution is stirred for 24 h at room temperature.

Sol 2: a sol is prepared comprising 30 mol % tetramethoxysilane, 45 mol % 3-glycidoxypropyltrimethoxysilane, 5 mol % 3-aminopropyltriethoxysilane, 10 mol % aluminum tri(sec.-butoxide) and 10 mol % zirconium tetrapropoxide. For hydrolysis, one mol of water is used, in total, per mol of alkoxy residue which is capable of being hydrolyzed. The time for hydrolysis amounts to 2 h at room temperature.

0.5 g sol 2 is slowly added, drop by drop, to sol 1 with cooling by means of ice. Filtration is then carried out by means of a filter (pore size 0.45 µm) and the solvent is distilled off at normal pressure.

The highly viscous resin is applied to PA6 foil by means of a spiral doctor-bar (50 µm). The layer is cured for 3 h at 130° C.

Table 1 shows the permeability, with respect to water vapor at 23° C. and 85% relative humidity, in Examples 1 to 5 of various embodiments.

TABLE I

| Coating (Applied to PA6*) | Coating Thickness (µm) | Permeability** (g/m² d) |
| --- | --- | --- |
| Uncoated | 70 | 23.0 |
| ORMOCER coating Example 4, sol 2 | 8 | 20.0 |
| Embodiment of Example 1 | 25 | 5.9 |
| Embodiment of Example 2 | 20 | 6.1 |
| Embodiment of Example 3 | 25 | 6.9 |
| Embodiment of Example 4 | 25 | 6.4 |
| Embodiment of Example 5 | 25 | 5.8 |

*PA6 = Polyamide 6 foil
**Permeability to water vapor at 23° C. and 85% humidity

What is claimed is:

1. Coating material on the basis of liquid crystalline polysiloxanes, characterized by the feature that they have been obtained via the co-condensation of organosilicon compounds selected from the group consisting of mesogenous silanes, polysiloxanes, and combinations thereof, which are capable of being hydrolyzed, with sols that are prepared by hydrolytic condensation of at least one organofunctional silane, which is capable of being crosslinked, optionally in the presence of a condensation catalyst and/or an additive.

2. Coating material in accordance with claim 1, characterized by the feature that the mesogenous silane, which is capable of being hydrolyzed, is defined by general formula I $$R_{3-m}R''_{m}Si-(CH_2-CH_2-CH_2)_n-X \quad (I)$$

in which
R=groups which are capable of being hydrolyzed including hydrogen, halogen, alkoxy, acyloxy, alkylcarbonyl, alkoxycarbonyl, or $NR'_2$ with
R'=hydrogen, alkyl or aryl
R" is a $C_1$–$C_{20}$ alkyl, either straight chain or branched.

8

X=a mesogenous molecular residue
m=0–2
n=1–25.

3. Coating material in accordance with claim 1, characterized by the feature that the co-condensate has been obtained via the addition of 5 to 99 mol % of the organosilicon compounds, which are capable of being hydrolyzed and which are prepared by pre-hydrolysis and condensation, to 95 to 1 mol % of the sol.

4. Coating material in accordance with claim 1, characterized by the feature that the co-condensate has been obtained via the addition of 5 to 99 mol % of the organosilicon compounds, which are capable of being hydrolyzed and which are prepared by pre-hydrolysis and condensation, to 95 to 1 mol % of the starting silane, which is used for the preparation of the sol, and a subsequent sol/gel process.

5. Coating material in accordance with claim 1, characterized by the feature that the co-condensate has been obtained via the addition of 5 to 99 mol % of the organosilicon compounds, which are capable of being hydrolyzed, to 95 to 1 mol % of the sol and subsequent co-condensation.

6. Coating material in accordance with claim 1, characterized by the feature that the co-condensate has been obtained via the addition of 5 to 99 mol % of the organosilicon compounds selected from the group consisting of mesogenous silanes, polysiloxanes, and combinations thereof, which is capable of being hydrolyzed, to 95.to 1 mol % of the starting silane, which is used for the preparation of the sol, and a subsequent sol/gel process.

7. Coating material in accordance with claim 2, characterized by the feature that the mesogenous molecular residue X is selected from derivatives of cyclohexane including the phenyl esters of cyclohexylcarboxylic acid, cyclohexyl phenyl esters, cyclohexyl phenyl ethers, cyclohexylbenzenes, cyclohexyl esters of cyclohexylcarboxylic acid, and dicyclohexyl derivatives, derivatives of stilbene, derivatives of the phenyl ester of benzoic acid, benzylidene-aniline, derivatives of azobenzene, derivatives of azoxybenzene, alkyl and alkoxy derivatives of biphenyl, Schiff's bases, steroids including derivatives of cholesterol and cholestane.

8. Coating material in accordance with claim 2, characterized by the feature that the co-condensate has been obtained via the addition of 5 to 99 mol % of the organosilicon compounds, which are capable of being hydrolyzed and which are prepared by pre-hydrolysis and condensation, to 95 to 1 mol % of the sol.

9. Coating material in accordance with claim 7, characterized by the feature that the co-condensate has been obtained via the addition of 5 to 99 mol % of the organosilicon compounds, which are capable of being hydrolyzed and which are prepared by pre-hydrolysis and condensation, to 95 to 1 mol % of the sol.

10. Coating material in accordance with claim 2, characterized by the feature that the co-condensate has been obtained via the addition of 5 to 99 mol % of the organosilicon compounds, which are capable of being hydrolyzed and which are prepared by pre-hydrolysis and condensation, to 95 to 1 mol % of the starting silane, which is used for the preparation of the sol, and a subsequent sol/gel process.

11. Coating material in accordance with claim 7, characterized by the feature that the co-condensate has been obtained via the addition of 5 to 99 mol % of the organosilicon compounds, which are capable of being hydrolyzed and which are prepared by pre-hydrolysis and condensation, to 95 to 1 mol % of the starting silane, which is used for the preparation of the sol, and a subsequent sol/gel process.

* * * * *